(12) United States Patent
Durmaz et al.

(10) Patent No.: US 9,707,259 B2
(45) Date of Patent: Jul. 18, 2017

(54) MAGNETIC DIFFUSIONAL PATCH

(71) Applicant: METUAS MEDIKAL SAGLIK HIZ-METLERI DANISMANLIK IHRACAT ITHALAT LIMITED SIRKETI, Cankaya, Ankara (TR)

(72) Inventors: Tuba Calik Durmaz, Ankara (TR); Mehmet Sorar, Ankara (TR)

(73) Assignee: Metuas Medikal Saglik Hizmetleri Danismanlik Ihracat Ithalat Limited Sirketi, Cankaya, Ankara (TR)

( * ) Notice: Subject to any disclaimer, the term of this patent is extended or adjusted under 35 U.S.C. 154(b) by 245 days.

(21) Appl. No.: 14/190,197

(22) Filed: Feb. 26, 2014

(65) Prior Publication Data
US 2014/0179982 A1 Jun. 26, 2014

Related U.S. Application Data

(63) Continuation of application No. PCT/TR2012/000163, filed on Oct. 2, 2012.

(30) Foreign Application Priority Data

Oct. 3, 2011 (TR) .................. 2011 09756
Aug. 31, 2012 (TR) .................. 2012 09991

(51) Int. Cl.
| | | |
|---|---|---|
| *A61N 2/00* | (2006.01) | |
| *A61K 36/28* | (2006.01) | |
| *A61N 2/06* | (2006.01) | |
| *A61K 9/70* | (2006.01) | |
| *A61K 36/185* | (2006.01) | |
| *A61K 36/328* | (2006.01) | |
| *A61K 36/53* | (2006.01) | |
| *A61K 36/71* | (2006.01) | |
| *A61K 36/87* | (2006.01) | |

(52) U.S. Cl.
CPC .............. *A61K 36/28* (2013.01); *A61K 9/703* (2013.01); *A61K 36/185* (2013.01); *A61K 36/328* (2013.01); *A61K 36/53* (2013.01); *A61K 36/71* (2013.01); *A61K 36/87* (2013.01); *A61N 2/002* (2013.01); *A61N 2/06* (2013.01)

(58) Field of Classification Search
CPC .................................. A61K 8/97; A61Q 19/00
USPC ............... 600/9, 15; 604/289, 304, 307, 308
See application file for complete search history.

(56) References Cited

U.S. PATENT DOCUMENTS

| | | | | |
|---|---|---|---|---|
| 1,748,470 | A * | 2/1930 | Domizlaff | A61F 13/0273 602/76 |
| 4,489,711 | A * | 12/1984 | Latzke | A61F 13/02 600/15 |
| 4,588,400 | A * | 5/1986 | Ring | A61L 15/28 424/447 |
| 6,319,942 | B1 * | 11/2001 | Perricone | A61K 8/0208 514/440 |
| 8,591,961 | B2 * | 11/2013 | Widgerow | 424/725 |
| 2002/0082279 | A1 * | 6/2002 | Schultz | A61K 8/922 514/330 |
| 2003/0031699 | A1 * | 2/2003 | Van Antwerp | A61K 31/436 424/423 |

(Continued)

*Primary Examiner* — Samuel Gilbert
(74) *Attorney, Agent, or Firm* — Merchant & Gould P.C.

(57) ABSTRACT

The invention relates to a diffusional magnetic patch, which is a medical device for application in the treatment of disc hernia and sports injuries, including a special formulation that acts mechanically with diffusional effect.

4 Claims, 1 Drawing Sheet

(56) References Cited

U.S. PATENT DOCUMENTS

| | | | |
|---|---|---|---|
| 2007/0254947 A1* | 11/2007 | Takiguchi | A61K 31/05 514/458 |
| 2008/0279902 A1* | 11/2008 | Luria | A61K 8/02 424/401 |
| 2009/0056734 A1* | 3/2009 | Bacon | A61K 8/34 132/202 |
| 2009/0068128 A1* | 3/2009 | Waddington | A61K 8/673 424/59 |
| 2009/0092691 A1* | 4/2009 | Spannagel | A61K 9/107 424/744 |

* cited by examiner

MAGNETIC DIFFUSIONAL PATCH

CROSS-REFERENCE TO RELATED APPLICATION

This is a Continuation application of PCT Patent Application PCT/TR2012/000163 filed on Oct. 2, 2012, which claims the priority benefit of Turkish Patent Application No.: 2011/09756 filed on Oct. 3, 2011 and Turkish Patent Application No.: 2012/09991 filed on Aug. 31, 2012, which are hereby incorporated herein by reference.

TECHNICAL FIELD

Said invention, namely the magnetic diffusional patch, relates to a gel-form medical device, a medical device with mechanical effect performing continuous release, a medical device with mechanical effect performing controlled release, a medical device with mechanical effect performing sustained release, a medical device with mechanical effect in micro-sponge and/or patch form, massage oil, massage kit, softening cream, said device being considered within the scope of the medical devices and intended for use in the treatment of the disc hernia and sports injuries.

BACKGROUND

At the present, more than half of the world's total population has ages suitable for working, i.e. they are aged in the range of 20-64 years. Considering the increase in the population that the working people are liable to look after, the health of the adult population at the working ages becomes more important. Today, there are a great many of health problems that affect the working adults. Of these, lumbar pains are one of the most significant, taking into account the labor loss they create and the economic losses they cause. The lumbar pain has a high prevalence in the range of 30-50 years, which is considered to be the productive age range. This condition restricts the activities of the individuals, leading to labor losses. Lumbar pain, which is indicated to be the disease ranked $2^{nd}$ in terms of leading to the greatest extent of labor loss, after the respiratory tract infections, is frequently encountered in the industrialized societies. For example, it is indicated to be a health problem which 85% of the individuals in USA encounter in a period in their life. Although the economic data for Turkey are not exact, in USA, the lumbar pain is ranked the $2^{nd}$ among the reasons for consulting a physician, the $3^{rd}$ among the surgical practices, and the $5^{th}$ among the causes for hospitalization. The expenses associated with the lumbar pain alone are estimated to be approximately 80 million dollars annually. (Nilay AYDOĞAN, Patients' needs for information at the stage of discharge after being exposed to a surgical operation due to Lumbar Disc Hernia, Hacettepe University Institute of Health Sciences, Nursing Program in Surgical Diseases, Master of Science Thesis).

In USA, the lumbar pains are ranked the $4^{th}$ after angina pectoris, hypertension and diabetes mellitus, in terms of health expenses, and an annual expense of 90.24 dollars is made per working individual. In addition, the lumbar pain-associated annual production loss is reported to be 28 million dollars and a workday loss of 149 million is estimated on a yearly basis. (Sema Pai, MPH, Lakshmi J., Sundaram, MIA, MPH Low Back Pam: An Economic Assessment in The United States Orthop Clin N Am 35, 1-5, 2004.)

In a study conducted at Çukurova University Faculty of Medicine for determining the characteristics of the cases involving lumbar pain, an assessment of the diagnosis for the cases has revealed that the disc diseases are ranked the first with a rate of 27.7% (Kozanoğlu, M.E., Demirkesen, A., Adam, M., Sarpel, T., Goncu, K., Characteristics of our Cases Involving Lumbar Pain, Çukurova University Faculty of Medicine Journal, Volume: 22, No.: 4, 264267, 1997).

A large proportion of the patients complaining about the lumbar pain are known to be afflicted with disc herniation. In the studies performed, the lumbar disc herniations (LDH) are indicated to account for 90% of all the disc herniations.

Herniation is a condition in which the entirety or a part of an organ bulges out of a cavity, sheath or the region where it is required to be positioned as per the usual anatomic structure. Intervertebral disc herniation is the condition in which the nucleus pulposus protrudes outwards from the annulus fibrosus.

Disc hernia is the name given to the disease, which emerges from the pathological changes occurring in the shape and contents of discus intervertebralis as a result of the causes other than infection or tumor. Discus intervertebralis is the structure, which is present between the vertebras and is primarily responsible for the absorption and distribution of the axial loads imposed on the columna vertebralis. Lumbar disc herniations (LDH) comprise the most frequently encountered group among the disc herniations. And the majority of the cases are comprised by the lower lumbar disc herniations.

LDH is treated in three ways; conservative, surgical and chemonucleolysis. The basis of the conservative treatment is to protect the herniated disc from excessive strains and to promote the healing by way of fibrosis. The treatments employed for this purpose may be listed as bed rest, drug therapy, local injection, traction, manipulation and the back schools where the training is provided on the proper use of the body mechanics. Failure of the conservative treatment to be effective, aggravation of the pains, and development of the neurological deficits necessitate the surgery.

The treatment methods currently employed:

The first group of treatment methods comprises the surgical operations.

Surgical interventions carried out for this purpose are the procedures practiced using the discectomy, laminectomy and microsurgery techniques.

The disadvantages of this method are the individual's absence from the work for at least 1 week and the continued risks of anesthesia and operation during the convalescence (in case the patient has a chronic disorder, such as hypertension, diabetes mellitus, etc.). The phase of repetition of the treatment also brings about many problems.

Despite the advances in recent years in the surgical techniques for LDH, some complications may emerge in the postoperative period.

In addition to the general postoperative complications, these may be enumerated as neurovascular injuries (0.4%), cerebrospinal fluid leak (2.2%), disc space infection (1.5%), intermeningeal adherences and infection (1.6%), recurrence of a pain as severe as in the preoperative period (14%). The incidence of complications following the surgical intervention performed as a result of LDH is reported to be 5.5%. (Nilay AYDOĞAN, Patients' needs for information at the stage of discharge after being exposed to a surgical operation due to Lumbar Disc Hernia, Hacettepe University Institute of Health Sciences, Nursing Program in Surgical Diseases, Master of Science Thesis).

Among the complications that might develop, the most significant one is the possibility for the recurrence of the herniation. It is known that, despite the surgical treatment applied, LDH usually recurs at a rate of 5-15% and that the technique employed, the level of herniation, inappropriate patient selection and the failure of the patient to act in compliance with the body mechanics in the postoperative period are effective in the development of recurrence. (Nilay AYDOĞAN, Patients' needs for information at the stage of discharge after being exposed to a surgical operation due to Lumbar Disc Hernia, Hacettepe University Institute of Health Sciences, Nursing Program in Surgical Diseases, Master of Science Thesis).

Human vertebral discs undergo multi-functional biochemical and morphological changes with time. Along with the degeneration increased with passing age, there is also observed an increase in the frequencies of the disc herniation and lumbar pain. The degenerated discs spontaneously cause an increase in the amount of many inflammation mediators that play a role in degenerative processes. There is present a need for the studies aimed at clarifying the relations between the disease and these degenerative processes. Intervertebral discs are the non-vascular tissue elements surrounded by extracellular matrix. Although the annulus fibrosus has a predominantly collagen structure, the central cells thereof are rich in proteoglycans. It is believed that, along with aging, the decrease in the proteoglycans is a critical factor in the degeneration of the intervertebral discs. Many inflammation mediators are associated with the degeneration of the intervertebral discs, including nitric oxide (NO), interleukins, prostaglandin E2 (PGE2) and tumor necrosis factor alpha (TNF-alpha). In the studies conducted, many of these were shown to play a role in the deformation of the joint cartilage (Podichetty 2007).

It was shown that the hernial discs lead to a significant increase in the activity of metalloproteinase and the levels of NO, PFE2 and interleukin-6 as compared to the control discs, in the culture medium (Kang 1996). NO production occurs along with the degenerative lumbar problems, resulting from the increased NO synthase activity in the cerebrospinal fluid. However, the mechanisms of the inflammatory mediators including NO in these disorders have not been able to be definitely understood. Consecutive degenerative events lead the structural defects and the loss of normal motion (Podichetty 2007).

The second group of treatment methods comprise the physiotherapy.

The disadvantage of this method is the necessity for the individual to spare a certain time for traveling to the hospital for treatment for at least 10-15 days and also to spare a time period of at least 3-4 hours per day for resting in the post-treatment period.

The third group of treatment methods comprises the relaxation of the region by using the muscle relaxant medicines.

The disadvantage of this method is that such medicines, which are orally administered, trigger the stomach disorders, if any, of the individuals, due to the acidic properties thereof, once they have been dissolved in the stomach medium.

The studies conducted in the recent years indicate that the natural antioxidants, including also the volatile compounds available in the plants, may prevent the oxidative damage and thus, they may be protective against the processes of inflammatory cell aging (Khanna et al., 2007) and the neurodegenerative damage (Fusco et al).

Terpenoids, which constitute a great proportion of the chemical contents of the essential oils, pass through the cell membrane owing to their low molecular weight and thus, they induce different biological activities including the anti-inflammatory and anticholinesterase effects ([Chao et al, 2005], [Kulisic et al., 2007] and [Loizzo et al., 2007]).

The section provided above, which mentions the known aspects of the invention by way of the studies in the literature, is a description of the secondary effect intended to support the treatment of the pain resulting from the inflammation and edema that occur especially in the cases of disc hernia and sports injuries.

SUMMARY OF THE INVENTION

Figure 1:
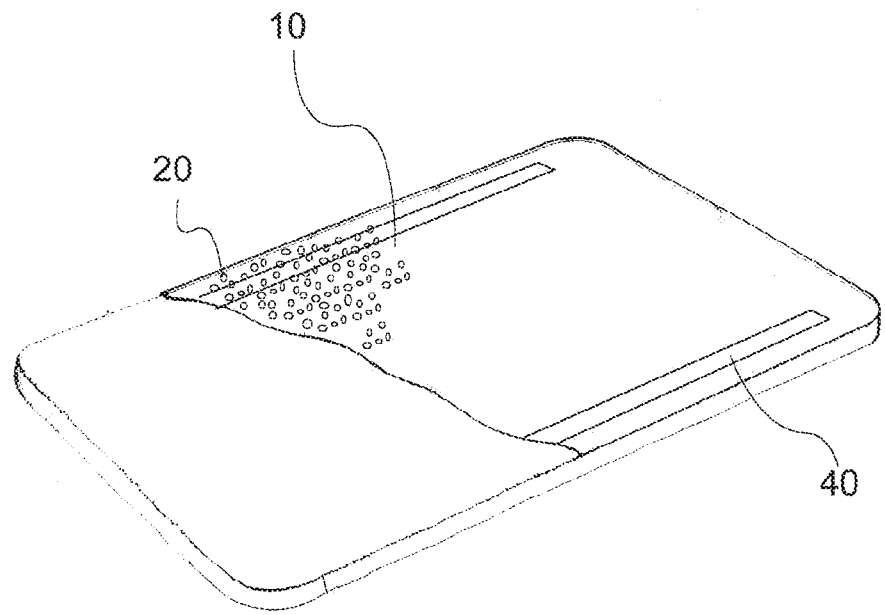
FIG. 1 is a top perspective view of a magnetic diffusional patch according to an example embodiment of the present disclosure.
Figure 2:
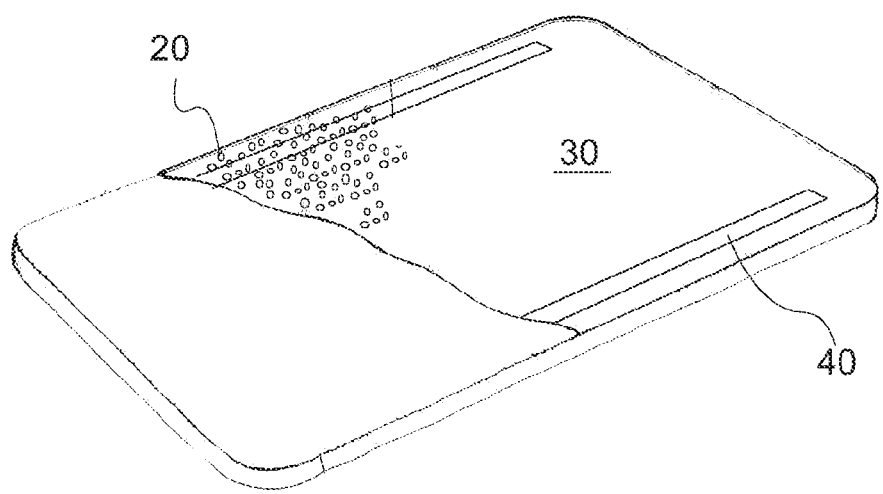
FIG. 2 is a bottom perspective view of the magnetic diffusional patch shown in FIG. 1.

The present invention according to an example embodiment relates to a diffusional patch to be used preferably in the treatment of a hernia. The diffusional patch includes an oil combination providing the liquid to be ejaculated from the hernia by means of a difussional effect arising from osmotic pressure by penetrating into the hernia. The oil combination includes the following components by weight percentage:

| Component | Amount(%) |
|---|---|
| Sodyum Laury Sulfate | 1-10 |
| Dextrin Palmite Derivatives | 1-10 |
| Cety Alcohol | 1-10 |
| Stearyl Alcohol | 5-10 |
| Liquid Vaseline | 1-20 |
| Paraffin | 1-30 |
| Lanoline | 1-10 |
| Water | 1-10 |
| Oleum *Nigellae Sativae* | 1-20 |
| Oleum Origani | 1-20 |
| Oleum Laurie Expressum | 1-30 |
| Oleum Limonis | 1-15 |
| Oleum Chamomillae | 1-30 |
| Balsammum Meccae | 1-30 |
| Oleum *Vitis Vinifera* | 1-10 |
| Styrax Liquidus | 1-30 |

The diffusional patch also includes a primary medical material within which the oil combination is placed.

According to a second example embodiment, the present invention relates to an oil combination to be used in the treatment of a hernia. The oil combination includes the following components by weight percentage:

| Component | Amount(%) |
|---|---|
| Sodyum Laury Sulfate | 1-10 |
| Dextrin Palmite Derivatives | 1-10 |
| Cety Alcohol | 1-10 |
| Stearyl Alcohol | 5-10 |
| Liquid Vaseline | 1-20 |
| Paraffin | 1-30 |
| Lanoline | 1-10 |
| Water | 1-10 |
| Oleum *Nigellae Sativae* | 1-20 |
| Oleum Origani | 1-20 |
| Oleum Laurie Expressum | 1-30 |
| Oleum Limonis | 1-15 |

-continued

| Component | Amount(%) |
|---|---|
| Oleum Chamomillae | 1-30 |
| Balsammum Meccae | 1-30 |
| Oleum *Vitis Vinifera* | 1-10 |
| Styrax Liquidus | 1-30 |

DETAILED DESCRIPTION OF THE INVENTION

Owing to said invention, the disadvantages of all these methods will be overcome and the treatment will be realized within 24 hours. The diffusional magnetic patch is a product with superiority over the existing treatments for disc herniation and athletic injuries, since it provides a rapid and mechanical healing owing to the diffusion effect created. The anti-inflammatory and anti-edema effect defined as per the known aspect of the technology and the science supports the diffusional mechanical effect as a secondary effect.

The patient group on which said invention is to be employed includes especially the patients with lumbar and cervical disc herniation and the edematous sports injuries.

The magnetic diffusional patch with dimensions 20*15 cm with respect to the determined disc space is applied via the skin in such a way that the diseased disc space will remain exactly at the center of the patch; and for the sports injuries, if there is no open wound, the patch is applied via the skin exactly on the region with edema. Following the application to the patient, the application is monitored along with the bed rest.

The magnetic diffusional patch according to the invention consists of 3 main structures:

Structure: The primary medical material having micro-sponge feature, specially woven, with high absorption capacity and possible buffering zones in the lower and upper sections thereof.

2. Structure: A structure, which is in solid-semisolid form at room temperature, but becomes free under the influence of the body temperature upon contact with the body and releases the substances that will exhibit the mechanical effect, said structure being obtained by way of gelling with dextrin palmitate derivative.

The density of the oils is lower than that of water, particularly because of the terpenoids that constitute a great proportion of the chemical ingredients of the oils. Disc hernia is a gelose structure with a water ingredient of 90% (d>1). In the edematous tissue formed in the sports injuries, the intercellular fluid density is increased (d≥1). Upon the application of the magnetic diffusional patch according to the invention, the oils that separate from the gelling and carrying agent by means of the body temperature assume different duties and move towards the region with a high fluid content. Among these oils, the pore expanding effect of Oleum limonis is utilized. Oleum chamomilla and Sytrax Liquidus are volatile oils, being the oils that first arrive at the fluid region and form a saturated buffer zone owing to their ability of rapid movement. Upon the arrival of also the other oils at the herniated disc and at the edematous region with increased intercellular fluid in cases of sports injuries, there is formed a volumetrically significant region with a density lower than that of water, immediately behind the buffer zone.

3. Structure: This structure is positioned on the right and left side of the microfiber structure, and depending on the form of application, it may also be formed by way of scattering magnetic flakes into the semisolid-solid form exhibiting mechanical effect or it may be designed so that it may be externally applied along with the administration.

The below-mentioned vegetable oils contained by the product according to the invention create anti-edema, anti-inflammatory and analgesic effect due to the secondary effect that support the primary mechanical effect, owing to the synergic effect they exhibit. The below-mentioned vegetable oils are listed by weight percentage of the total.

Sodium lauryl sulfate 1-10, Dextrin Palmitate Derivatives 1-10, Cetyl Alcohol 1-10, Stearyl alcohol 5-10, Liquid vaseline 1-20, Paraffin 1-30, Lanoline 1-10, Water 1-10, Oleum nigellae sativae 1-20, Oleum origani 1-20, Oleum lauri expressum 1-30, Oleum limonis 1-15, Oleum chamomillae 1-30, Balsamum Meccae (i.e., Balm of Gilead) 1-30, Oleum Vitis Viniferae 1-10, Styrax Liguidus 1-30. The auxiliary substances for the formulation may be decreased, increased or replenished according to the local properties.

The vegetable oils contained by the product according to the invention create anti-edema, anti-inflammatory and analgesic effect that support the secondary effect, owing to the synergic effect they exhibit.

The medical device in the form of oil, ointment, pad, cream, gel, the medical device with mechanical effect performing continuous release, the medical device with mechanical effect performing controlled release, the medical device with medical effect performing sustained release and the micro-sponge and/or patch-form medical device formulations with mechanical effect, all of which contain said vegetable oil combinations, may be prepared. In addition, the formulation may be used by way of being impregnated into a carrier matrix or a medical textile product with high absorptivity, and it is also possible to achieve a long-time skin contact by enabling the formation of a mass upon the preparation of a waxy formation.

For all these formulations, it is possible to use any thickening, bulking and carrying chemical material that will not interact with the herbal mixture.

The contents and the effects of the oils present as ingredients of said invention are listed below.

It was shown in the experimental studies that thymoquinone, which is present within oleum nigellae sativae at a proportion of about 25%, induces anti-inflammatory response by differentiating the cellular lipid peroxidation with the aid of eicosanoids and also is able to suppress the induced arthritis with the aid of collagen. It was shown that thymoquinone blocks the cyclooxygenase (COX) and lipooxygenase enzymes and inhibits the synthesis of thromboxane and leukotriene B4 from eicosanoids. Application of thymoquinone in the experimental animals causes a reduction in the levels of the pro-inflammation cytokines TNF-alpha and interleukin (IL)-1beta, whose levels are increased in case of rheumatoid arthritis, and said application thus decreases the severity of the disease.

Origanum species is a plant containing anti-inflammatory components such as rosmarinic acid, oleanolic acid and ursolic acid (Shen D 2010). When used in the treatment of colitis in the experimental animals, Origanum was shown to cause a reduction in the levels of proinflammatory cytokines such as IL-1β, IL-6, GM-CSF and TNF-α. There are opinions that the essential oils obtained from Origanum could be effective in the prevention of the neurodegenerative disorders (Loizzo et al, 2009). In the studies using the activated human THP-1 macrophages for cellular modeling, it was observed that the fractions obtained from Origanum reduce the synthesis of the proinflammatory cytokines TNF-α, IL-1β and IL-6, while they increase the production of the anti-inflammatory cytokine 1L-10.

Laurus nobilis is employed topically in the traditional medicine for the relief of the rheumatoid pains. The anti-inflammatory effect of α-pinene, β-pinene and sabine, which are among the primary components of laurel oil, was shown by experimental models. In addition, 4-terpineol was shown to suppress the inflammation mediators in the activated human monocytes (Hartet al., 2000). In a study conducted on experimental animals, the analgesic and anti-inflammatory effects of the laurel oil were shown by formalin and tail reflex tests, and the effects were indicated to be statistically comparable to the non-steroidal anti-inflammatory drugs morphine and piroxicam. The anesthetic and muscle relaxant properties of eugenol and methyl eugenol as the ingredients of the laurel oil were also shown (Sayyah 2003). Further, the laurel oil exhibits antibacterial characteristic and owing to this characteristic, it is believed that it could extend the shelf life of the products (Ramos 2011).

Oleum limonis increases the transdermal passage of various molecules without leading to skin irritation, and due to this property, it is used in different dermal combinations.

Chamomillae is a plant that has been used for centuries in different cultures for treating eczema, ulcer, got, neuralgia and rheumatoid pains. Its therapeutic activity is attributed to various flavonoid components and flavones (apigenin, luteolin) and the flavone derivative compounds (quercetin, patuletin) contained in its structure. Chamomile was approved by German Commission E for oral use in various inflammatory diseases and ulcer, and for dermal use in various skin diseases and inflammation diseases. The researches conducted showed that chamomile is a selective COX inhibitor with anti-inflammatory effects. Moreover, its anti-inflammatory effect on the macrophages was shown, through the suppressive effect thereof on the inducible nitric oxide synthase (iNOS) expression and NO production. The application of chamomile, in addition to suppressing the NO production, has a significant blockage for the NO levels induced by IL-1β, IL-6 and TNFα.

Although there is limited research on the gum (Oriental Sweet Gum) obtained from the plant Liquidambar orientalis (sweet gum tree), which grows epidermically in our country, it is believed to possess anti-inflammatory, antiseptic and antibacterial effect due to the resins it contains.

Said invention also provides magnetic effect. According to general information, it is known that the magnetic effect was used in 3. Century B.C. by the Greek physicists for the treatment of the arthrolith by means of magnetized metals, and in the Middle Age by the doctors for the treatment of gout, baldness and intoxication by means of the magnets. As in said times of history, the static electricity-charged metals/magnets are also used today as a support for a great many treatments, since they have the capacity to form a continuous energy flow.

Even though there are not sufficient clinical studies, it is stated that the magnets regulate the blood flow, increase the amount of oxygen in the body, increase the lymph drainage and relax the muscles. The magnet results in a positive effect on the humans in terms of healing.

3 steps are performed in the production of the magnetic system included in said invention.

1. Step: Production of the herbal softening oil mixture

In this step, the mixture is prepared with a system in which the hot and cold processes follow each other, using the thickening agents according to the field of application.

2. Step: Formation of the carrier portion

The magnetic bands positioned in a way to be located on the right and left side of spinal cord are placed horizontally by leaving the packaging gaps on the right and left side of the polyvinyl material, which also used in the food production. Instead of the magnetic band, the magnetic flakes may also be positioned on the form where the oil mixture is produced.

Pressure is applied by means of compressor system to this dual system formed, thereby forming the reservoir region to carry the product. The softening mixture is spread and applied for being positioned in the middle of the magnetic bands in the reservoir formed. It is covered with a protective and permeable material.

When the product is positioned on the carrier by the application of spreading without forming the reservoir, it is covered with a sterile permeable material such as cotton, and is secured on the 2. portion.

3. Step: The stage of closing the package

In the 2. Step, in order to prevent the direct contact between the body and the product, it is entirely covered with gauze compress and is closed with folio material, which is also used in the food production. The adhesive used in the closing procedure is a material, which is activated by heat and is used in the food products. It is also possible to perform closing by heat without using the adhesive material.

The diffusional structure available in the product according to the invention provides mechanical effect along with the diffusional treatment support in order to assist the magnetic application. Diffusional structure contains the vegetable oils along with the particular carrier thereof. These oils support the resting state of the regional muscles and also provide support in increasing the lymph drainage.

Annulus fibrosus in the collagen structure surrounding the nucleus pulposus has the membrane characteristic that enables the structure referred to as discus inter vertebralis to be fed by way of diffusion. Beginning from 12 years of age, the vascular feed of discus inter vertebralis ends and it continues to be fed by way of diffusion. When the discus inter vertebralis becomes herniated, annulus fibrosus, along with nucleus pulposus, also becomes severely herniated or the integrity of annulus fibrosus may be lost and it may become torn. In both cases, the membrane characteristic of annulus fibrosus becomes corrupted. Oleumcitrus, available as an ingredient of the medical device according to the invention, features the ability to mechanically expand the pores. The diffusional magnetic patch carries its components up to the discus inter vertebralis region. The low molecular weight oils within the product components benefit from the corruption of the membrane characteristic of herniated annulus fibrosus to become diffused into the herniated nucleus pulposus. The low molecular weight oils, utilizing the advantage of having a smaller structure and of moving more rapidly, pass physically and completely mechanically from the membrane with corrupt permeability into the herniated nucleus pulposus region. The low molecular weight oils reaching this region become diffused into the intrinsic distance through the collagenous polar spaces in the structure of herniated nucleosus pulposus. In this way, they physically cause a temporary increase in the volume of herniated discus inter vertebralis. In case said physical volume increase results in increased pressure on the nerve root, it may cause a temporary increase in the pain in the patients during the first 24 hours. Because the diffused oils mechanically disrupt the membrane permeability and they reduce the osmotic pressure in the environment where they are present, the water in the intercellular region that is available in the structure of herniated nucleus pulposus and that constitutes approximately 88% of this structure passes from the hypo osmotic portion into the zone that is more hyper osmotic as compared to itself, outside the herniated annulus fibrosus, by way of simple mechanical effect. In this way, herniated nucleus pulposus, about 88% of the total weight of which is comprised by the intercellular water, looses a great portion of its weight as a result of simple mechanical passage of water and thus, the pressure on the nerve root volumetrically (mass) disappears. As a result, the clinical symptoms resulting from the pressure imparted by the herniated discus inter vertebralis on the nerve root disappear.

Said vegetable oil-containing combinations may be prepared in gel, cream, pad, wax form in a way to remain on the skin for at least 12 hours, in micro-sponge and/or patch form performing continuous release, performing controlled release, performing sustained release, by way of being combined with carrier matrix or textile product or of being integrated to a device, said combinations thus being prepared by way of configuring the same in pharmaceutical, medical or medicinal device format.

The product according to the invention may also be applied by targeting the part immediately over the edematous region in the sports injuries.

As a result, the magnetic diffusional patch is a product, which allows an effective noninvasive treatment method that may be attempted before the patient is taken into operation, for the lumbar disc patients with pain resistant to medical treatment and physiotherapy. Its mechanical effect formed by the diffusion mechanism is secondarily supported by the anti-inflammatory and anti-edema effects and, also in cases of sports injury, it provides the treatment support within short time and at low cost, in a way not to lead to labor loss.

The invention claimed is:

1. A method for treating a hernia, the method comprising applying a diffusional patch onto skin exactly on a region with a hernia, the diffusional patch consisting of magnetic bands positioned oppositely on the diffusional patch so as to be adapted to be positioned on opposite sides of the hernia, and an oil combination that causes a liquid to be ejaculated from the hernia by means of a difussional effect arising from osmotic pressure by the oil combination penetrating into the hernia, the oil combination comprising a solid-semisolid gel at room temperature, the oil combination configured to be released from the gel state upon influence of body temperature, the oil combination consisting of the following components by weight percentage:

| Component | Amount |
| --- | --- |
| Sodyum Lauryl Sulfate | 1-10 |
| Dextrin Palmitate Derivatives | 1-10 |
| Cety Alcohol | 1-10 |
| Stearyl Alcohol | 5-10 |
| Liquid Vaseline | 1-20 |
| Paraffin | 1-30 |
| Lanoline | 1-10 |
| Water | 1-10 |
| Oleum *Nigellae Sativae* | 1-20 |
| Oleum Origani | 1-20 |
| Oleum Laurie Expressum | 1-30 |
| Oleum Limonis | 1-15 |
| Oleum Chamomillae | 1-30 |
| Balsammum Meccae | 1-30 |
| Oleum *Vitis Vinifera* | 1-10 |
| Styrax Liquidus | 1-30 | and a primary medical material, the oil combination is placed therein.

2. The method of claim 1, wherein said primary medical material comprises of micro-sponge feature.

3. The method of claim 1, wherein the primary medical material is a woven material.

4. A method for treating a hernia, the method comprising applying an oil combination to skin exactly on a region with a hernia, the oil combination consisting of the following components by weight percentage:

| Component | Amount |
| --- | --- |
| Sodyum Lauryl Sulfate | 1-10 |
| Dextrin Palmitate Derivatives | 1-10 |
| Cety Alcohol | 1-10 |
| Stearyl Alcohol | 5-10 |
| Liquid Vaseline | 1-20 |
| Paraffin | 1-30 |
| Lanoline | 1-10 |
| Water | 1-10 |
| Oleum *Nigellae Sativae* | 1-20 |
| Oleum Origani | 1-20 |
| Oleum Laurie Expressum | 1-30 |
| Oleum Limonis | 1-15 |
| Oleum Chamomillae | 1-30 |
| Balsammum Meccae | 1-30 |
| Oleum *Vitis Vinifera* | 1-10 |
| Styrax Liquidus | 1-30. |

* * * * *